United States Patent [19]

Pyke

[11] Patent Number: 5,144,845
[45] Date of Patent: Sep. 8, 1992

[54] ADHESIVE TESTING DEVICE

[75] Inventor: John A. Pyke, Orpington, England

[73] Assignee: Molins PLC, Miltin Keynes, Great Britain

[21] Appl. No.: 645,490

[22] Filed: Jan. 24, 1991

[30] Foreign Application Priority Data

Jan. 25, 1990 [GB] United Kingdom ............... 9001744

[51] Int. Cl.⁵ .............................................. G01N 3/08
[52] U.S. Cl. ..................................... 73/827; 73/150 A
[58] Field of Search ............... 73/827, 150 A; 156/64, 156/378; 414/222

[56] References Cited

U.S. PATENT DOCUMENTS

| | | | |
|---|---|---|---|
| T916,005 | 11/1973 | Dolen et al. | 73/150 A |
| 4,645,401 | 2/1987 | Hopkins et al. | 414/222 |
| 4,893,513 | 1/1990 | Schroeder et al. | 73/827 |

FOREIGN PATENT DOCUMENTS

1077058 7/1967 United Kingdom .

Primary Examiner—Jerry W. Myracle
Attorney, Agent, or Firm—Antonelli, Terry, Stout & Kraus

[57] ABSTRACT

An adhesive testing device includes a movable carriage (2) carrying a substrate (4) to which adhesive is applied by an applicator wheel (32). The carriage is brought to rest opposite the anvil (46) carrying another substrate. The substrates are pressed together and the force required subsequently to separate them measured. In a preferred arrangement the anvil is carried by a beam (48) bearing a strain gauge (60). The carriage is preferably inverted during its movement to the applicator wheel: this allows it to have its operative surface uppermost initially for ease of application of the substrate. Various parameters (e.g. periods between operations, speed of the carriage, temperature of adhesive and/or anvil) may be varied to simulate conditions in a packing machine.

19 Claims, 7 Drawing Sheets

ADHESIVE TESTING DEVICE

This invention relates to a device for testing adhesives, particularly for testing the strength of a bond formed by the adhesive between particular substrates.

In packing machinery, e.g. machines for forming or wrapping cigarette packets, there are typically required processes for securing together surfaces (e.g. of packet flaps) where the conditions under which the seal is made are constrained by the machine process. For example, in such machinery the time during which surfaces may be pressed together (possibly with application of heat) to create an adhesive bond may be relatively short, and it is obviously desirable that an adhesive should be capable of reliably maintaining the bond when the pressure on these surfaces is released. It is an object of the invention to provide a device capable of simulating various conditions found on a manufacturing machine in which an adhesive may be used, and to test the strength of an adhesive bond formed under such conditions. The measured strength of a bond may then be compared with that considered necessary for satisfactory sealing of the surfaces in use.

According to the invention an adhesive testing device includes a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and carriage, and means for measuring the force required to separate the anvil and carriage to obtain a measurement of the strength of the adhesive bond between the substrates.

Preferably the device includes means for controlling the time between application of adhesive and the bringing together of the substrates between the carriage and anvil, means for controlling the time during which the carriage and anvil are pressed together, and/or means for controlling the time between release of pressure between the carriage and anvil and the subsequent separation of the carriage and anvil. In addition, preferably the pressure applied between the anvil and carriage is controllable. Preferably, also, the anvil may be heated to a controlled temperature.

Furthermore, the adhesive applying means preferably includes means for varying the amount, thickness, pattern, and/or temperature of the adhesive applied to the substrate.

The means for separating the anvil and the carriage may impose a separating force which is substantially normal to the substrates, or substantially parallel to the substrates, or in any other direction tending to separate the substrates.

In a preferred arrangement where the separating force is substantially normal to the substrates the anvil is mounted on a substantially horizontal beam which includes a strain gauge for producing a measurement of force required to separate the adhesive bond between the substrates. The beam may be pivoted and subject to a moment, e.g. provided by a rotary cam, tending to separate the anvil from the carriage. Where the separating force is substantially parallel to the substrates, so that shear strength of the adhesive bond is tested, the anvil may comprise a rotary member restrained by resilient means the deflection of which provides a measure of shear strength. Thus, after the bond is formed between the substrates, a substantially tangential force may be applied to the carriage, which force is resisted by the resilient means as long as the adhesive bond holds.

The means for urging the carriage and anvil together may comprise means for urging the anvil towards the carriage, for example an air clamp, with the anvil conveniently located substantially directly below the carriage. The carriage may move along a substantially horizontal path between the adhesive applying means and the position in opposition to the anvil.

In a further preferred arrangement the carriage is movable along a substantially horizontal path past the adhesive applying means and so that the substrate receives adhesive whilst the carriage is moving along said path. By arranging for adhesive to be applied to a moving substrate, the application of adhesive may also simulate that existing in many types of machinery: the speed of movement of the carriage during which adhesive is applied could be varied. Where the adhesive applying means includes a driven member (e.g. an applicator wheel) the carriage and driven member may be synchronised so that they have similar speeds during application of adhesive. Means may be provided for heating the adhesive to a desired operating temperature, e.g. so that hot melt adhesive may be used.

In a further preferred arrangement, in which the carriage is movable along a substantially horizontal path, the carriage includes a surface carrying the substrate, said surface being uppermost in an initial position on a path along which the carriage moves, but subsequently inverted so that the surface is lowermost when it is in opposition to the anvil. By arranging for the surface of the carriage on which the substrate is mounted to be uppermost initially, the securing of the substrate (which may be by double-sided adhesive tape) to the surface is facilitated. Adhesive may be applied to the substrate while the substrate is facing upwards and/or while it is facing downwards. Thus, conveniently, adhesive may be supplied by spray or jet downwards onto the substrate in a first portion of the path of the carriage, and may be applied upwards, e.g. by an applicator wheel having its lower periphery in a reservoir of adhesive, where the carriage is inverted in a second portion of said path.

The movable carriage may comprise a body having a surface for carrying a substrate, a threaded bore arranged to co-operate with a threaded drive shaft, and first and second longitudinally-offset lateral guide members (e.g. rollers) arranged to co-operate with a track which has first and second portions along which the carriage is reversibly movable respectively with the surface uppermost and lowermost (i.e. with the carriage in mutually inverted positions on said first and second portions), said first and second portions of the track being separated by at least one gap which allows passage of a guide member during inversion of the carriage through 180° about the axis of said shaft, said inversion being obtained by transmission of rotation to the carriage by said shaft, rotation of the carriage at other times being resisted by engagement of at least one of said guide members with said track.

It will be appreciated that the substrates fixed to the carriage and anvil are selected with a view to being tested with the adhesive: in other words, it will be recognised that the material of the substrates may have a significant effect on the performance of the adhesive. Commercially available double-sided adhesive tape, used to fix the substrates to the carriage and anvil, has a bond strength sufficiently greater than adhesives as typically used in packing machinery for its use not to affect results obtained by the device.

The invention will be further described, by way of example only, with reference to the accompanying diagrammatic drawings, in which.

Figure 1:
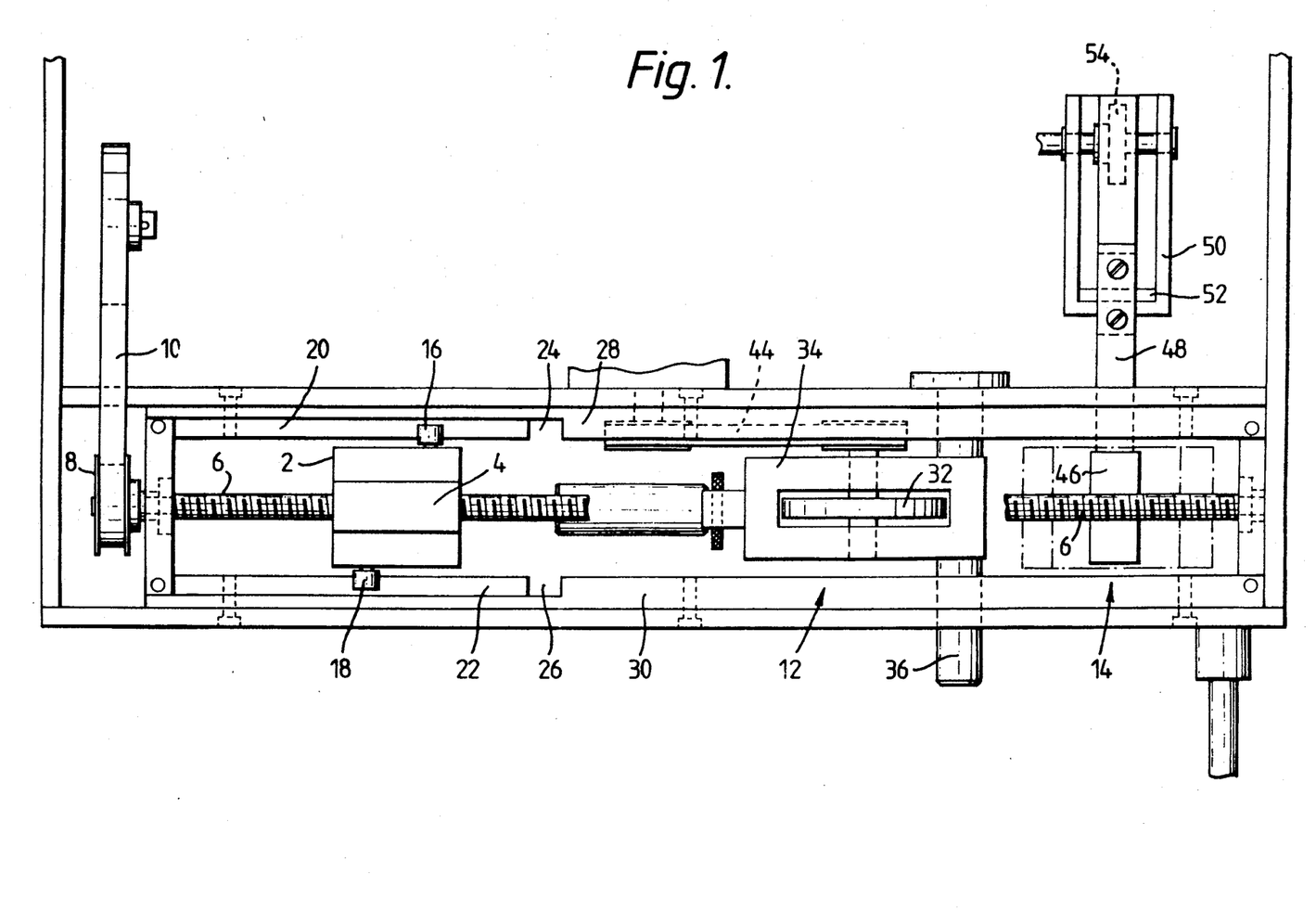
FIG. 1 is a plan view of an adhesive testing device.
Figure 2:
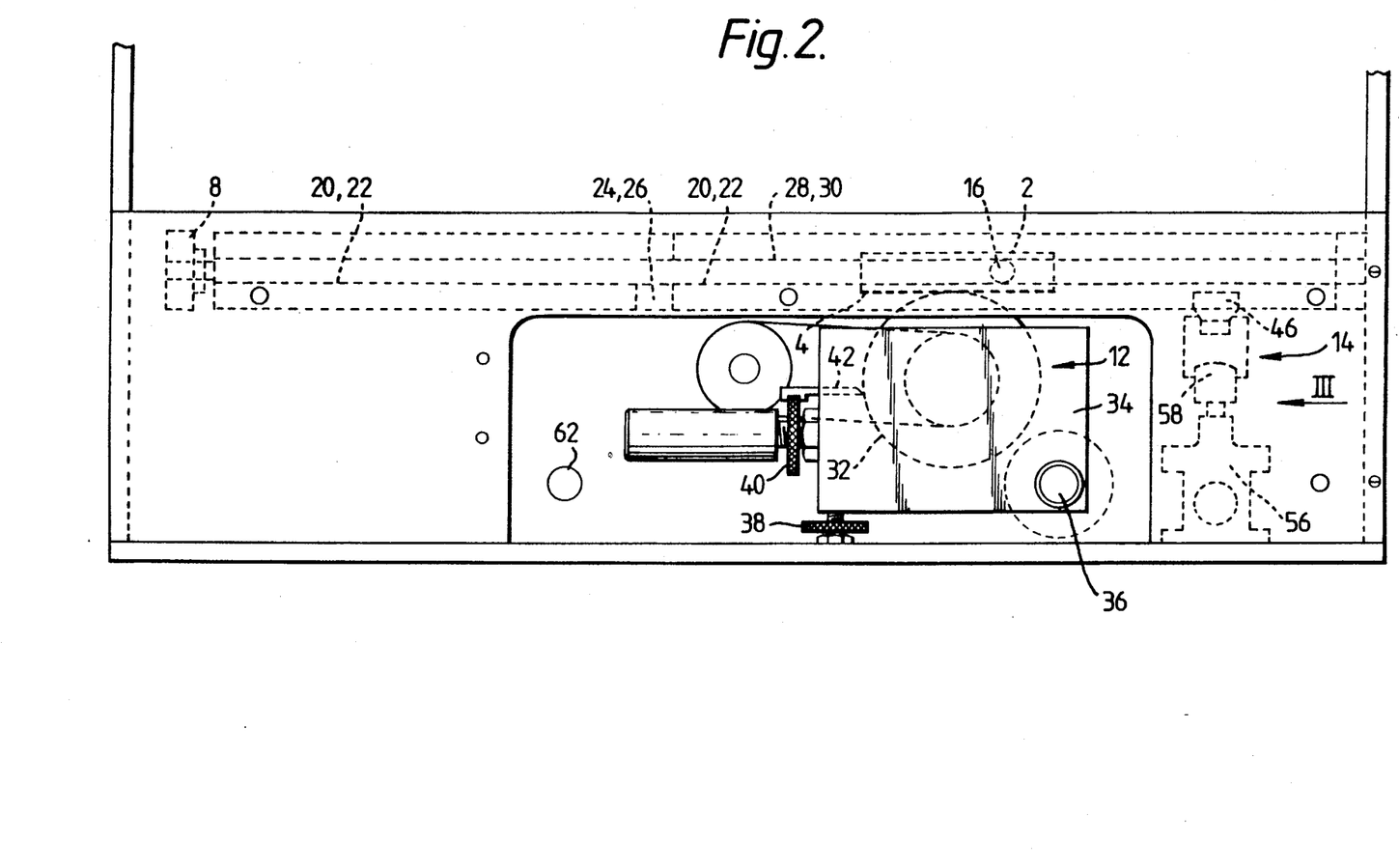
FIG. 2 is a side view of the device of FIG. 1.

FIGS. 1 and 2 show an adhesive testing device including a carriage 2 for supporting a substrate 4 arranged to receive a coating of adhesive. The substrate 4 may comprise a strip of card, hoard, paper, film, foil or other relatively flat material with which it is desired to test the adhesive. The substrate 4 may be secured to the carriage 2 by means of double-sided adhesive tape.

The carriage 2 has an internal threaded bore engaged with a drivable threaded rod 6. Rotation of the rod 6, by means of a pulley 8 and driven belt 10, serves to reversibly convey the carriage 2 along the rod 6 between its initial position (as shown in FIG. 1) and an adhesive application position 12 and an adhesive testing position 14.

The carriage 2 has offset lateral rollers 16, 18 which, in the position shown in FIG. 1 are respectively in engagement with stationary lower rails 20, 22. Upstream of the adhesive application position 12 there is a short gap 24, 26 in each of the lower rails 20, 22 respectively, beyond which gap upper rails 28, 30 are respectively spaced above the lower rails by a distance slightly exceeding the diameter of the rollers 16, 18. Downstream of the gaps 24, 26 the respective rails 20, 28 and 22, 30 therefore form a track for the rollers 16 and 18.

Rotation of shaft 6 in an anti-clockwise direction (as viewed from pulley 8) causes carriage 2 to advance to the right (as viewed in FIG. 1), the tendency of the carriage to rotate about the shaft 6 being resisted by the roller 16 engaging the rail 20. When the roller 16 reaches the gap 24, however, the carriage 2 performs a rotation through 180° about the axis of shaft 6, further rotation being prevented by engagement of the roller 18 with the rail 20. Subsequent advancement of the carriage 2 causes the roller 16 to pass into the track formed between rails 22 and 30: this prevents the carriage 2 performing any further rotational movement when the roller 18 reaches the gap 24.

As shown in FIG. 2, the substrate 4 is therefore on the underside when the carriage 2 reaches the adhesive applicator position 12. The adhesive applicator comprises an applicator wheel 32 rotatably supported within a magazine 34, the lower portion of which forms a reservoir for adhesive. The magazine 34 is secured to the structure of the device by a threaded bolt incorporating a handle 36 and includes a height adjusting screw 38, whereby the height of the wheel 32 relative to the carriage 2 may be adjusted, and a screw adjustment 40 for a scraper 42 for controlling the thickness of the film of adhesive on the wheel 32. A belt drive 44 is provided for rotating the applicator wheel 32.

Figure 3:
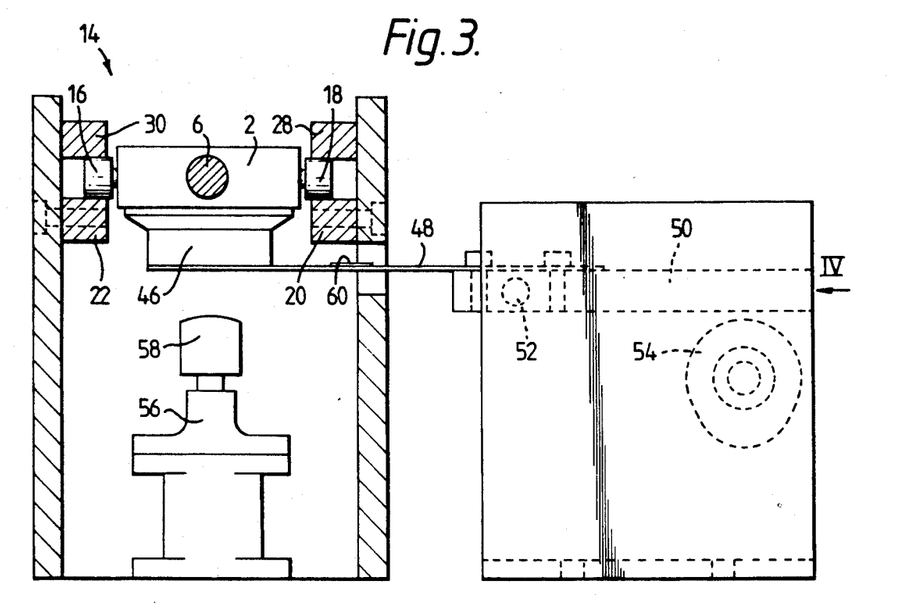
FIG. 3 is a view in the direction of arrow III in FIG. 2.
Figure 4:
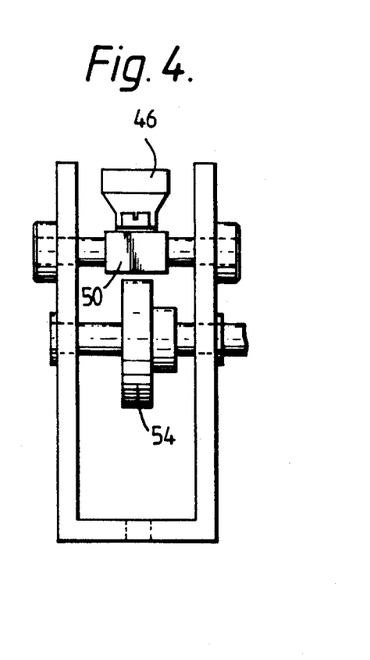
FIG. 4 is a view in the direction of arrow IV in FIG. 3.
Figure 5:
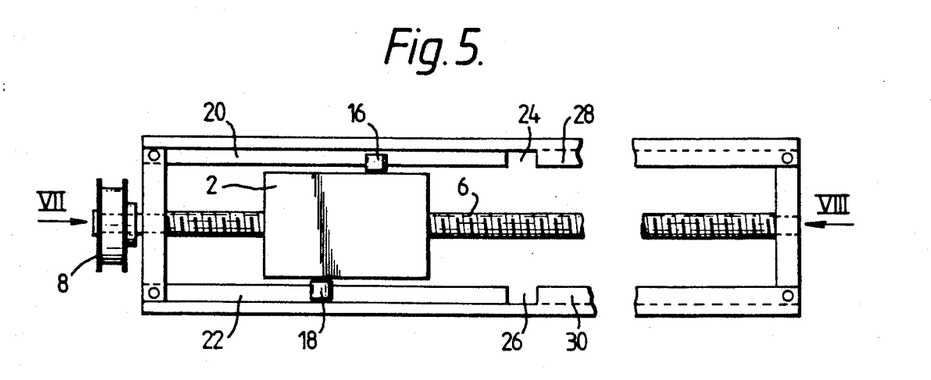
FIG. 5 is a plan view of a carriage and track assembly of the device of FIG. 1.
Figure 6:
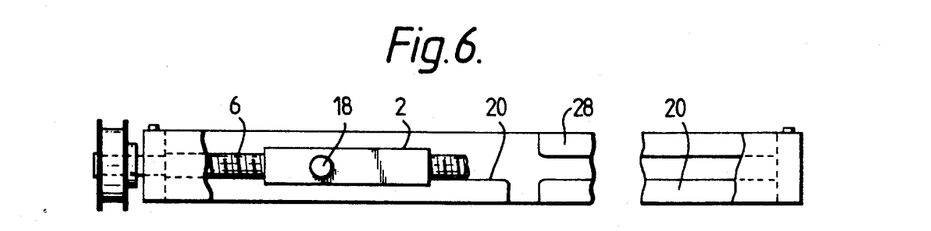
FIG. 6 is a side view of the assembly of FIG. 5.
Figure 7:
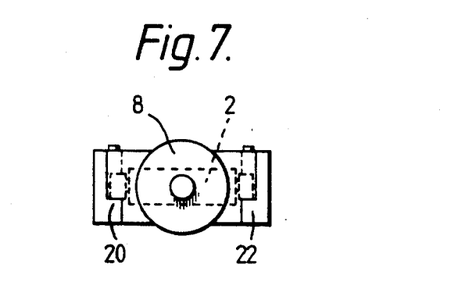
FIG. 7 is an end view in the direction of arrow VII in FIG. 5.
Figure 8:
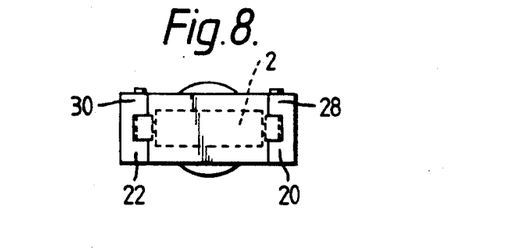
FIG. 8 is an end view in the direction of arrow VIII in FIG. 5.

At the adhesive testing position 14, shown also in FIGS. 3 and 4, the carriage 2 comes to rest above an anvil 46 carrying on its upper surface a further substrate consisting of a material with which the adhesive is intended to be tested. The substrate on the anvil 46 may (but need not) be of a similar material to that of the substrate 4, and may be similarly secured to the anvil by means of double-sided adhesive tape. The anvil 46 is connected to one end of a spring steel beam 48, the other end of which is bolted to a rigid beam 50. The composite beam 48, 50 is pivotally mounted at 52 and the beam 50 may be engaged by a rotatable cam 54 tending to raise the beam. A strain gauge 60 is mounted on the spring steel beam 48.

An air clamp 56, having a piston 58, is mounted directly beneath the anvil 46. The piston 58 is movable to engage the anvil 46 and apply variable upwards pressure on the anvil.

In operation, the carriage 2 is initially at rest in the position shown in FIG. 1. A suitable substrate 4 is applied to the carriage 2 and also to the anvil 46, and a suitable adhesive is placed in the magazine 34. The drive to the rod 36 is then connected, causing the carriage 2 to move to the right, typically at a speed of 25 metres/minute. Inversion of the carriage 2 takes place when the roller 16 reaches the gap 24 and subsequently the carriage passes over the applicator wheel 32, which is driven by the pulley drive 44 at a peripheral speed corresponding to the linear speed of the carriage 2. The substrate 4 thus receives a pattern of adhesive, depending on the nature of the wheel 32. Subsequently the carriage 2 comes to rest above the anvil 46. After a predetermined variable time (the "open" time) the air clamp 56 is operated to move the piston 58 against the anvil 46 to press the anvil against the carriage, thereby applying pressure to the two substrates and sandwiched adhesive. The pressure applied to the anvil 46 is variable, by varying the air pressure supplied to the air clamp 56, and the air pressure is applied for a predetermined variable time (the "closed" time). Subsequently the pressure applied by the piston 58 is released and after a further predetermined variable time (the "dwell" time) the drive to the cam 54 is operated to slowly rotate the cam (at about 5 rpm). so that the beam 5 is raised thereby applying a downward force on the spring steel beam 48, which force is transmitted to the anvil 46 and resisted by the adhesive bond between the substrate on the anvil and the substrate 4 on the carriage 2. The cam 54 is capable of producing a 5 mm lift of the beam 50 which, with a spring steel beam 48 typically of 2.5 mm thickness, produces an opening force capable of breaking the adhesive bond between the substrates. The strain gauge 60 measures the maximum deflection of the beam 48 just before the adhesive bond breaks.

The "open", "closed", and "dwell" times, referred to above, may be predetermined by control circuitry (e.g. including a microprocessor), and may be typically between 0.1 and 99.9 seconds. The pressure which may be applied to the anvil 46 by the piston 58 is in the range 0-55 p.s.i., but typically the applied pressure will be in the lower part of this range, e.g. 1-5 p.s.i. The strain gauge 60 may be connected through a suitable circuit (preferably including an analogue to digital converter and, again, a microprocessor) to provide a display of the force (or pressure) required to break the adhesive bond. In order to provide such a display in conventional units (e.g. of weight) the composite beam 48, 50 and strain gauge 60 arrangement is initially calibrated by means of a spring gauge or applied weights.

Other parameters which may be varied are quantity, thickness and type of adhesive, together with its method and pattern of application. The adhesive may be applied at ambient temperature or at a predetermined elevated temperature (e.g. for hot melt adhesive). For this purpose the magazine 34 may contain a heating element and temperature sensor, conveniently connected by leads (not shown) to a socket 62 (FIG. 2) for control and display of the adhesive temperature.

The anvil 46 includes a heating element for raising its temperature: the temperature of the anvil is monitored so that it may be raised to a desired value, preferably displayed on the device.

FIGS. 5-8 show the arrangement of the carriage 2, rollers 16, 18 and rails 20, 22, 28, and 30, without most of the additional parts shown in FIGS. 1 and 2.

Figure 9:
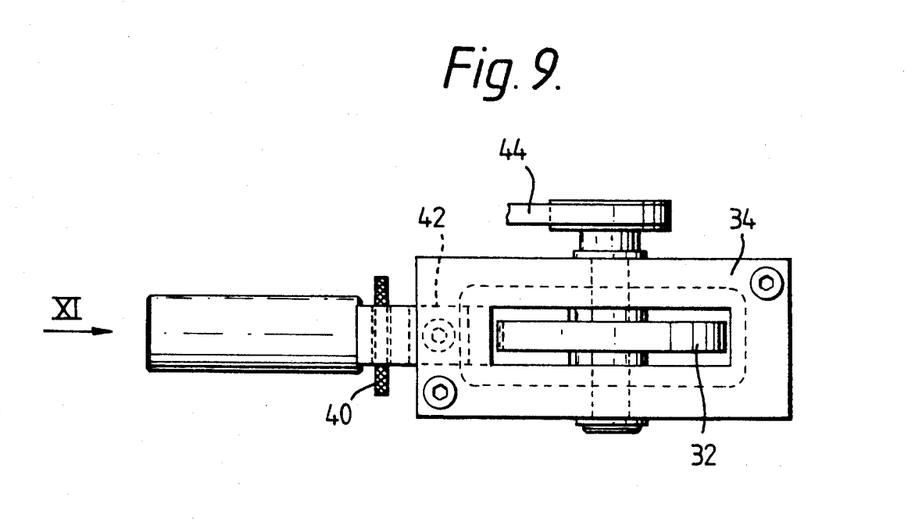
FIG. 9 is a plan view of an adhesive applicator for the device of FIG. 1.
Figure 10:
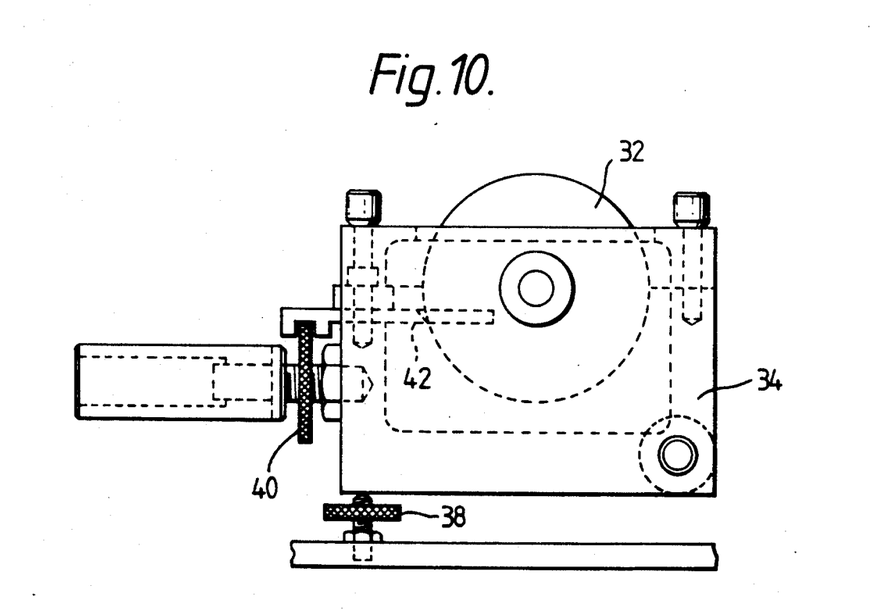
FIG. 10 is a side view of the applicator of FIG. 9.
Figure 11:
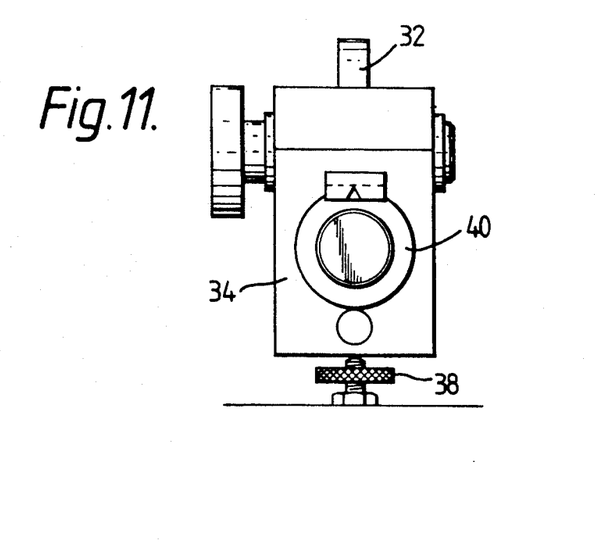
FIG. 11 is a view in the direction of arrow XI in FIG. 9.

FIGS. 9-11 show the adhesive applicator wheel 32 and associated parts in more detail than FIGS. 1 and 2.

Figure 12:
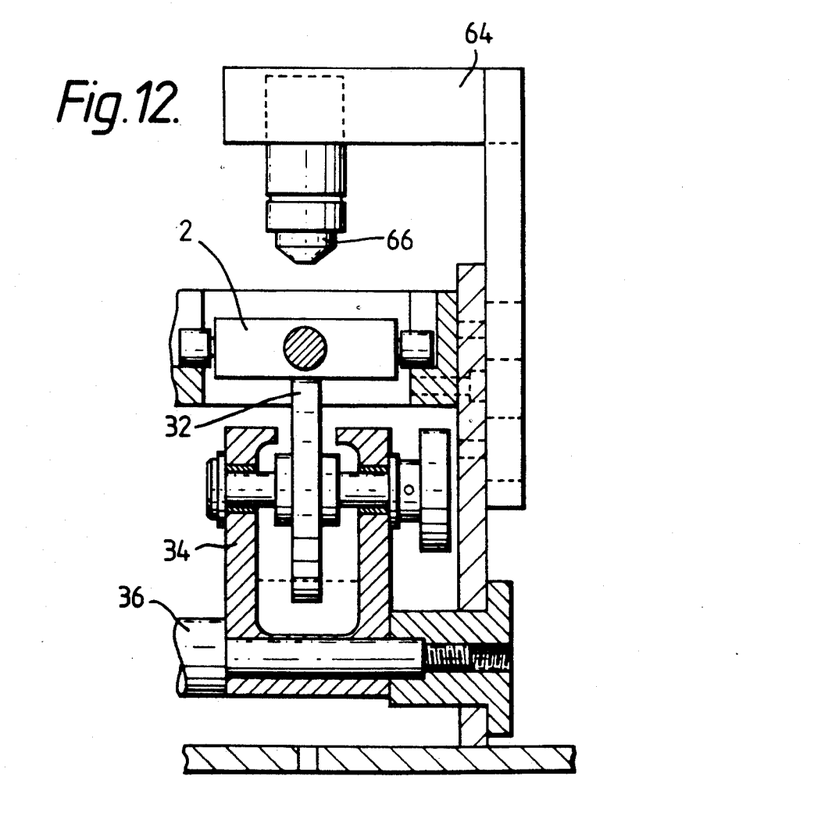
FIG. 12 is a transverse sectional view of a modified adhesive testing device incorporating two adhesive applicators.

FIG. 12 shows an overhead adhesive spray or jet unit 64 having a spray or jet head 66 for applying adhesive to the substrate 4 in the region of the device where the carriage 2 is arranged with the substrate uppermost, i.e. upstream of the gaps 24, 26 in the rails 20, 22 and at or adjacent the position of the carriage shown in FIG. 1. Thus, where the device incorporates a spray unit 64, controlled quantities of adhesive may be applied to the substrate 4 by the unit 64 and/or by the applicator wheel 32.

It will be appreciated that the carriage 2 may be stopped at the correct position above the anvil 46 by suitable photo-sensors which detect its position and stop the drive to the threaded shaft 6. After the bond strength test on the adhesive has been completed the drive to the shaft 6 is restarted, in the opposite direction, to return the carriage 2 to the position shown in FIG. 1. During its reverse movement no adhesive is required to be applied to the substrate by the wheel 32. The carriage 2 is automatically re-inverted, i.e. so that the substrate 4 is uppermost again, when the roller 16 reaches the gap 26. Drive to the shaft 6 is stopped when the carriage 2 reaches the position shown in FIG. 1 (as detected by a suitable photo-sensor).

Figure 13:
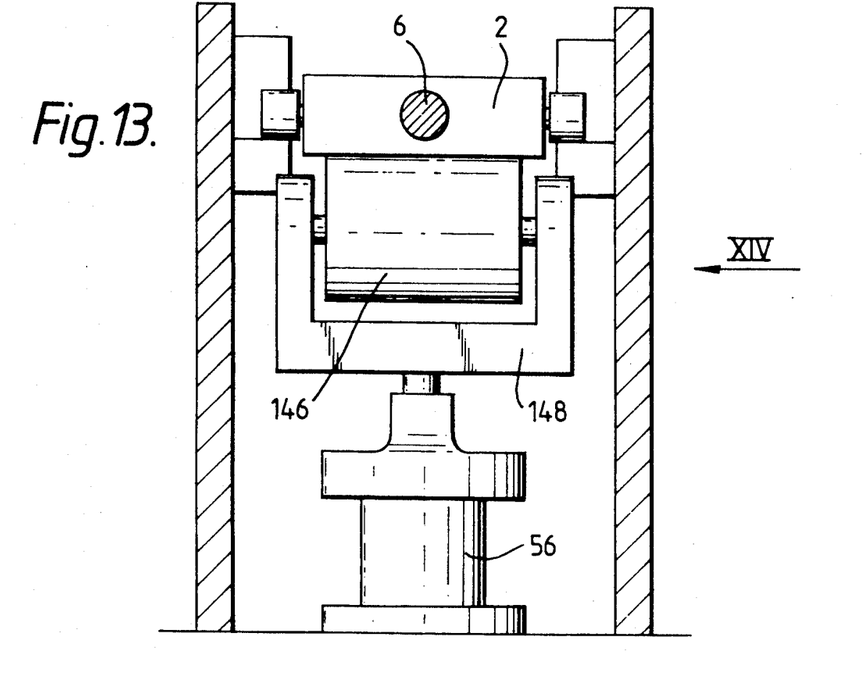
FIG. 13 is an end view of part of a further modified adhesive applicator device.
Figure 14:
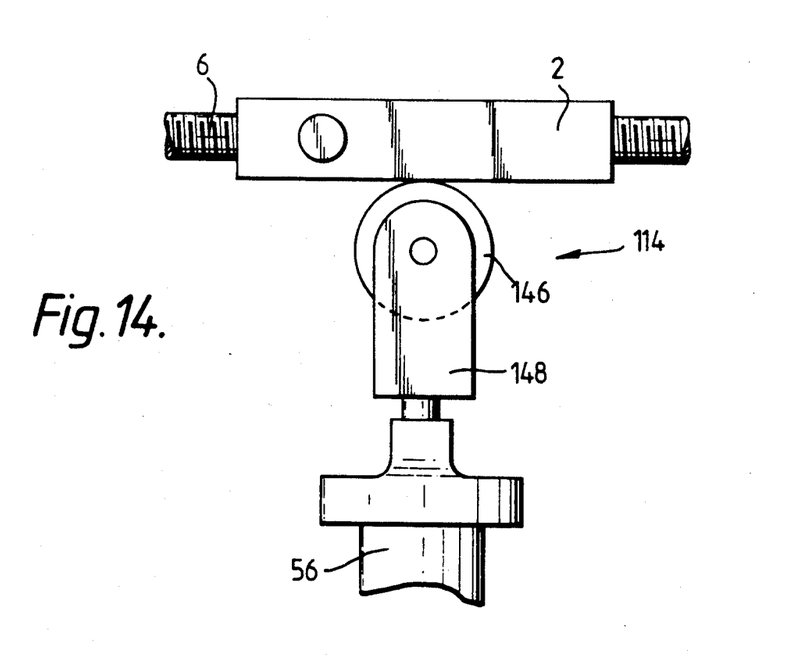
FIG. 14 is view in the direction of arrow XIV in FIG. 13.

The device so far described provides a measurement of bond strength in a direction substantially normal to the bonded substrates. For some adhesives and/or uses of adhesives a measure of shear strength, i.e. in a direction substantially parallel to the bonded substrates is appropriate. FIGS. 13 and 14 show an alternative adhesive testing position 114 in which the anvil 46 is replaced by an anvil roller 146 mounted on a yoke 148. The anvil roller 146 (which may be heated) carries a substrate which is pressed against the adhesive-carrying substrate on the underside of carriage 2. When it is required to test the shear strength of the adhesive bond the drive to the threaded shaft 6 is re-started (preferably in the reverse direction). A rotational force is thus transmitted to the anvil roller 146 by reason of the bond between the substrates. This rotation is resisted by an internal coiled spring. Deflection of the spring, corresponding to the rotation of the roller, is measured by a strain gauge. Maximum deflection occurs at maximum shear strength of the adhesive bond (i.e. when the bond between the substrates breaks). It will be appreciated that the strength of the internal coiled spring in the anvil roller 146 is selected so that the rotation of the roller before breaking of the adhesive bond is relatively small, in order to avoid any significant effect of forces tending to break the bond due to separation of the curved surface of the anvil roller from the flat surface of the carriage as the former rotates. Similarly, in order to avoid inaccurate readings, pressure is released from the air clamp 56 during testing so that measurement of shear strength of the adhesive bond is not masked by frictional effects due to pressure applied between the anvil roller 146 and the carriage 2. Instead of measuring deflection of an internal spring, deflection of the roller itself (or a shaft connected to it) may be measured directly (e.g. optically), or deflectioin may be measured of an an external spring, e.g. connected to a shaft on which the roller is mounted and resisting rotation of the shaft.

The adhesive testing position 114 may replace the position 14 in apparatus otherwise similar to that of FIG. 1.

I claim:

1. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the means for separating the anvil and the carriage includes means for imposing a separating force which includes at least a substantial component normal to the substrates, and including a beam on which the anvil is mounted, the beam carrying a strain gauge for producing a measurement of force required to separate the adhesive bond between the substrates.

2. A device as claimed in claim 1, wherein the beam is pivoted and the separating means includes means for pivoting the beam.

3. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the means for separating the anvil and the carriage includes means for imposing a separating force which includes at least a substantial component parallel to the substrates, wherein the means for urging the carriage and anvil together is arranged to apply controllable variable pressure between the anvil and carriage.

4. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the means for separating the anvil and the carriage includes means for imposing a separating force which includes at least a substantial component parallel to the substrates, wherein the anvil comprises a rotary member, and said measuring means includes means responsive to angular deflection of the member to provide a measure of shear strength of the adhesive bond.

5. A device as claimed in claim 3, wherein the adhesive applying means includes means for applying adhesive to the substrate on the movable carriage while said carriage is moving.

6. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the adhesive applying means includes means for applying adhesive to the substrate on the movable carriage while said carriage is moving, and wherein the adhesive applying means includes a driven member movable at the same speed as said carriage during application of adhesive.

7. A device as claimed in claim 6, including means for heating the anvil to a controlled temperature.

8. A device as claimed in claim 6, further including a source of adhesive, the adhesive applying means being arranged to transfer adhesive to the substrate from said source, and means for controlling the temperature of the adhesive in said source.

9. A device as claimed in claim 6, wherein the adhesive applying means includes means for varying the quantity of adhesive applied to the substrate.

10. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the adhesive applying means includes means for applying adhesive to the substrate on the movable carriage while said carriage is moving, and wherein the moving means includes means for varying the speed at which the carriage is moved past said adhesive applying position.

11. A device as claimed in claim 10, including means for controlling the time between application of adhesive and the bringing together of the substrates between the carriage and the anvil.

12. A device as claimed in claim 10, including means for controlling the time during which the carriage and anvil are pressed together.

13. A device as claimed in claim 10, including means for controlling the time between release of pressure between the carriage and anvil and the subsequent separation of the carriage and anvil.

14. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, including means defining a path for the carriage which passes said adhesive applying position and extends to said position in opposition to the anvil, and including means for inverting the carriage during its movement along said path.

15. A device as claimed in claim 14, wherein the carriage includes a surface carrying the substrate and is movable along a substantially horizontal path, said surface being uppermost on a first portion of said horizontal path and lowermost on a second portion of said path, said second portion including said position in opposition to the anvil.

16. A device as claimed in claim 15, wherein said means for applying adhesive includes spray means adjacent said first portion of said path.

17. A device as claimed in claim 15, wherein said adhesive applying means includes an applicator wheel engaging the substrate on said carriage in said second portion of said path.

18. An adhesive testing device comprising a movable carriage on which a substrate may be mounted, an anvil member on which another substrate may be mounted, means for applying adhesive to the substrate on the movable carriage, means for moving the carriage to a position in opposition to the anvil, means for urging the carriage and anvil together to bring the substrates and interposed adhesive together under pressure, means for subsequently separating the anvil and the carriage, and means for measuring the force required to separate the anvil and carriage to obtain a measurement of the strength of the adhesive bond between the substrates, wherein the movable carriage comprises a body having a surface for carrying a substrate, further including a threaded drive shaft, a threaded bore in said body and arranged to cooperate with said threaded drive shaft, and a track having first and second portions along which the carriage is reversibly movable with said surface uppermost and lowermost respectively, said body having first and second longitudinally-offset lateral guide members arranged to cooperate with said track.

19. A device as claimed in claim 18, wherein said first and second portions of the track are separated by at least one gap which allows passage of one of said guide members during inversion of the carriage through 180° about the axis of said shaft, said inversion being obtained by transmission of rotation to the carriage by said shaft, rotation of the carriage at other times being resisted by engagement of at least one of said guide members with said track.

* * * * *